United States Patent [19]

Buchholz et al.

[11] Patent Number: 5,725,881
[45] Date of Patent: Mar. 10, 1998

[54] SEMISOLID MIXTURES OF AMORPHOUS OLIGOMERS AND CRYSTALLINE POLYMERS BASED ON LACTIC ACID

[75] Inventors: Berthold Buchholz; Günther Entenmann, both of Ingelheim am Rhein, Germany

[73] Assignee: Boehringer Ingelheim KG, Ingelheim am Rhein, Germany

[21] Appl. No.: 329,344

[22] Filed: Oct. 26, 1994

Related U.S. Application Data

[63] Continuation of Ser. No. 143,421, Oct. 26, 1993, abandoned, which is a continuation of Ser. No. 965,452, Oct. 23, 1992, abandoned.

[30] Foreign Application Priority Data

Oct. 23, 1991 [DE] Germany ............................ 41 349 54

[51] Int. Cl.$^6$ ............. A61K 9/10; A61K 47/34; C08G 63/08
[52] U.S. Cl. ............. 424/486; 424/426; 525/450
[58] Field of Search ............. 424/426, 486; 525/450; 514/772.3

[56] References Cited

U.S. PATENT DOCUMENTS

| | | | |
|---|---|---|---|
| 4,766,182 | 8/1988 | Murdoch | 528/354 |
| 5,216,050 | 6/1993 | Sinclair | 524/310 |

*Primary Examiner*—Edward J. Webman
*Attorney, Agent, or Firm*—R. P. Raymond; M-E. M. Devlin; A. R. Stempel

[57] ABSTRACT

The present invention relates to semisolid mixtures of oligomers and/or polymers based on lactic acid, the preparation thereof and the use thereof as absorbable implants.

5 Claims, No Drawings

SEMISOLID MIXTURES OF AMORPHOUS OLIGOMERS AND CRYSTALLINE POLYMERS BASED ON LACTIC ACID

This is a continuation of application Ser. No. 08/143,421, filed Oct. 26, 1993 Abn, which is a continuation of application Ser. No. 07/965,452, filed Oct. 23, 1992 (abandoned).

The present invention relates to semisolid mixtures of oligomers and/or polymers based on lactic acid, the preparation thereof and the use thereof as absorbable implants. The term lactic acid for the purposes of the present invention includes both D- and L-lactic acid, with the result that the polymers or oligomers synthesised therefrom may contain D-, L- and D,L-lactic acid units. Absorbable materials of this kind which are tolerated by the body are suitable, inter alia, as absorbable implants for the following applications in the human or animal body:

- local haemostasis on the open bone by mechanical tamponade (bone wax)
- temporary filling of tissue defects (hard and soft tissue)
- plastic matrix material for the controlled release of active substances (e.g. antibiotics)

The physical properties of absorbable polyesters based on lactic acid are known from the literature [I. Engelbert and J. Kohn, Biomaterials 12 (1991) 292–304; A. U. Daniels et al., J. Appl. Biomat. 1 (1990) 57].

High molecular polyesters based on lactic acid are solids with no plastic deformability, irrespective of their composition, at ambient or body temperature. Depending on their steric unity they may have a partially crystalline morphology (poly(L-lactide), poly(D-lactide)), or they may be amorphous glassy solids (poly(D,L-lactide), poly(meso-lactide)).

In the low molecular range the mechanical and rheological properties are found to be highly dependent on the molecular weight and on the structure:

In the case of oligomers of DL-lactic acid which are not capable of crystallisation, the glass transition temperature rises as the molecular weight increases and at ambient temperature there is a gradual transition from a viscous fluid with a strong tendency to turn stringy, to glassy, brittle solids. Oligomers in a molecular weight range from about 500 to 2,000 (number average molecular weight) have both viscous and brittle characteristics.

In oligomers of L- or D-lactic acid the molecular weight influences the ability to crystallise and hence the consistency. With a molecular weight of less than about 400 the oligomers are amorphous. Their properties correspond substantially to those of the oligo(DL-lactic acids). Above a molecular weight of about 700 the condensation products crystallise very easily and form hard solids. In the median molecular weight range, at ambient temperature very slow crystallisation can be observed which can be accelerated by increasing the temperature. The consistency of these condensates thus depends to a considerable extent on the thermal pretreatment of the sample.

It has also been proposed in the literature to produce materials which have different characteristic profiles than the individual components by mixing various absorbable polyesters together.

Thus, mixtures of polymeric poly-(L-lactide) and poly-(D-lactide) with high molecular weight are known from U.S. Pat. Nos. 4,719,246, 4,766,182, 4,800,219 and 4,981,696. In these mixtures, stereocomplexes are present having a high melting crystalline phase and a slower degradation rate than the individual components.

European Patent Application 401 844 discloses mixtures of poly(L-lactide) and poly(D,L-lactide) with high molecular weight.

WO 90/01521 describes mixtures of polylactides which contain lactide or oligomeric lactides as plasticiser.

U.S. Pat. No. 4,440,789 describes the use of mixtures of polydioxanone and a second component as an absorbable bone wax. The second component may be a substance such as sesame oil, castor oil, isopropylpalmitate, polyethyleneglycol and copolymers of ethyleneglycol and propyleneglycol.

The published Canadian Application 12 60 488 proposes mixtures consisting of copolymers based on lactide together with glycolide and castor oil.

It is also known from the literature that copolymers with lower molecular weight of ε-caprolactone and δ-valerolactone have a waxy consistency and are suitable for use in active substance release systems [I. Imasaka et al., Int. J. Pharm. 68 (1991) 87].

U.S. Pat. No. 4,443,430 discloses copolymers of lactide and glycolide with lower molecular weight having a lactide content of between 30 and 70 mol-%, the molecular weight of the oligomers being in the range from 2000 to 2500.

EP 0 100 981 relates to absorbable waxes based on polyester oligomers and a process for preparing them. The molecular weight of the resulting polyester is regulated by the addition of alcohols, carboxylic acids or amines during polymerisation or polycondensation and its consistency is thereby influenced.

Published German Application 37 16 302 relates to the use of polyester oligomers of glycolic acid or lactic acid with glycerol as absorbable bone waxes.

Published German Application 38 25 211 discloses the addition of organic or inorganic salts for the purpose of improving the consistency of bone waxes prepared on the basis of oligomers of glycolic or lactic acid.

Finally, published German Application 38 26 915 describes mixtures of ceramic materials and polyester-oligomers of lactic or glycolic acid with mono- or polyfunctional carboxylic acids or alcohols as bone replacement materials.

However, the oligomers of lactic acid or glycolic acid known from the prior art have the disadvantage that—irrespective of the addition of other components such as dodecanol, ethyleneglycol or glycerol—they have a more or less viscous consistency at a relatively low molecular weight, with a consequent marked tendency to become ropey and inherently runny. However, as the molecular weights increase, the brittleness of the oligomers increases.

The aim of the present invention is to provide an absorbable material which is biocompatible with the body for the applications mentioned hereinbefore, which does not have the above-mentioned drawbacks and has a waxy to pasty consistency.

A further object of the present invention is to provide a material which is plastically deformable at ambient or body temperature, i.e. in a temperature range from about 20° to about 40° C.

According to the invention these objectives are achieved by means of mixtures of amorphous, viscous oligomers based on lactic acid with crystalline oligomers or polymers.

According to the invention, the blends are prepared by simple melt mixing, the temperature and mixing time required depending on the nature, proportions and molecular weights of the components used as well as the size of the batch. In order to prevent any possible thermal degradation during mixing, it is generally advantageous to keep the temperature as low as possible so as to obtain a homogeneous melt. The mixtures listed in the Examples show that at a temperature of up to 160° C. there is no measurable degradation. The GPC investigation carried out in Example 12 also shows that under the mixing conditions which prevail here there is no equilibration of the molecular weights, e.g. as a result of reactions of transesterification.

The properties of the mixtures which are relevant for application, such as consistency and speed of degradation, can be adjusted by a suitable choice of components, composition and molecular weights.

The oligomers or polymers used in the mixtures may be synthesised in a known manner by polycondensation of the corresponding lactic acids or by ring-opening polymerisation of the corresponding dilactones. In the case of polycondensation, there is no need to add a molecular weight regulator since the level of oligomerisation can easily be adjusted by ending the polycondensation when the desired level of dehydration is reached.

In order to prepare mixtures of oligomers and/or polymers based on lactic acid the procedure conveniently followed involves mixing the oligomers or polymers to be used for the mixture, which have been prepared by methods known per se, heating them until they melt, homogenising the melt and, after homogenising it, cooling it and isolating the semisolid mixture.

In order to prepare the blends the following polymers and oligomers are particularly suitable; any of the crystalline components can be combined with any of the amorphous components:

Crystalline oligomers or polymers:

oligo- and poly(L-lactide)

oligo- and poly(D-lactide)

copolymers and block-co-oligomers of L- and D-lactic acid statistical copolymers or oligomers of L- and D-lactic acid, the proportion of the particular foreign monomer being limited to a maximum of about 10% in order to achieve a crystalline structure.

Amorphous oligomers:

oligo(L-lactate)

oligo(D-lactate)

oligo(DL-lactate)

oligo(meso-lactate)

statistical co-oligomers based on D- and L-lactic acid as well as on D-, L-, DL- and meso-lactide co-oligomers based on lactic acid with monohydric alcohols—such as ethanol, propanol or isopropanol—or polyhydric alcohols—such as ethyleneglycol, propan-1,2-diol, propan-1,3-diol, glycerol, erythritol, sorbitol, mannitol, dulcitol—or carbohydrates—such as fructose, glucose, maltose—or hydroxycarboxylic acids—such as glycolic acid, β-hydroxypropionic acid, α-hydroxyvaleric acid, β-hydroxyvaleric acid, γ-hydroxyvaleric acid, δ-hydroxyvaleric acid—or polycarboxylic acids—such as malonic acid, succinic acid, glutaric acid, adipic acid—or hydroxycarboxylic acids—such as citric acid, tartaric acid or malic acid.

Of the numerous possible mixing combinations, mixtures of a viscous liquid L-lactide with low molecular weight with a crystalline L-lactide with higher molecular weight are preferred, since in this case hydrolysis generates only L-lactic acid, i.e. a substance native to the body. Such blends are structurally uniform and differ from conventionally produced oligomers or polymers of L-lactic acid by their broader and in some cases asymmetrical distribution of molecular weights. As can be seen from a comparison of Examples 4 and 12 (both samples have virtually the same mean molecular weight), the molecular weight distribution has a considerable influence on the crystallisation qualities and hence on consistency.

As already mentioned hereinbefore, crystalline polymers with a molecular weight of at least 500—preferably 600—are suitable for the preparation of the mixtures. The polymers may be both statistical as well as homo- or copolymers.

The present invention thus relates to oligomer or polymer mixtures consisting of a homopolymer of D- or L-lactic acid with a number average molecular weight in the range from 600 to 10000 and an amorphous, viscous oligomer based on lactic acid with a number average molecular weight of less than 500.

The invention relates in particular to the above-mentioned oligomer or polymer mixtures in which the homopolymer has a number average molecular weight in the range from 800 to 8000 and the oligomer based on lactic acid has a number average molecular weight of less than 400.

The invention preferably relates to the above-mentioned oligomer or polymer mixtures in which the homopolymer has a number average molecular weight in the range from 1500 to 6000 and the oligomer based on lactic acid has a number average molecular weight of less than 350.

The invention relates, most especially to oligomer or polymer mixtures in which the homopolymer has a number average molecular weight in the range from 1800 to 4000 and the oligomer based on lactic acid has a number average molecular weight of less than 350.

The present invention further relates to oligomer or polymer mixtures consisting of block-copolymers and block-co-oligomers of L- and D-lactic acid with a number average molecular weight in the range from 600 to 10000 and an amorphous viscous oligomer based on lactic acid with a number average molecular weight of less than 500.

The invention further relates particularly to the above-mentioned oligomer or polymer mixtures in which the copolymer has a number average molecular weight in the range from 800 to 8000 and the oligomer based on lactic acid has a number average molecular weight of less than 400.

The invention further relates, preferably, to the above-mentioned oligomer or polymer mixtures in which the copolymer has a number average molecular weight in the range from 1500 to 6000 and the oligomer based on lactic acid has a number average molecular weight of less than 350.

The invention also relates, particularly preferably, to oligomer or polymer mixtures in which the copolymer has a number average molecular weight in the range from 1800 to 4000 and the oligomer based on lactic acid has a number average molecular weight of less than 350.

The invention aim relates to oligomer or polymer mixtures consisting of a statistical copolymer of L- and D-lactic acid with a number average molecular weight in the range from 600 to 10000 and a content of L-lactic acid units of between 90 and 99% or 1 and 10% and an amorphous viscous oligomer based on lactic acid with a molecular weight of less than 500.

The invention also relates particularly to oligomer or polymer mixtures in which the statistical polymer of L- and D-lactic acid has a number average molecular weight in the range from 800 to 8000 and the oligomer based on lactic acid has a molecular weight of less than 400.

The invention also relates preferably to oligomer or polymer mixtures in which the statistical polymer of L- and D-lactic acid has a number average molecular weight in the range from 1500 to 6000 and the oligomer based on lactic acid has a molecular weight of less than 350.

The invention also relates most preferably to oligomer or polymer mixtures in which the statistical polymer has a number average molecular weight in the range from 1800 to 4000 and the oligomer based on lactic acid has a number average molecular weight of less than 350.

Furthermore, the present invention relates to above-mentioned oligomer or polymer mixtures, the oligomer containing units of L-lactic acid and/or D-lactic acid.

In addition, the invention particularly relates to oligomer or polymer mixtures in which the oligomer contains further units of the series of mono- or polyhydric alcohols and this alcohol preferably takes the form of ethanol, glycerol, mannitol, sorbitol, ethanediol, 1,3-propanediol or 1,2-propanediol.

The present invention also relates especially to oligomer or polymer mixtures, in which the oligomer contains further units from the series of hydroxycarboxylic acids and the hydroxycarboxylic acid is preferably glycolic acid, citric acid or tartaric acid.

In addition, the invention relates particularly to oligomer or polymer mixtures, in which the oligomer contains further units from the series of mono- or polyvalent carboxylic acids and the carboxylic acid preferably takes the form of acetic acid or a divalent $C_{3-8}$-carboxylic acid.

The present invention also relates to oligomer or polymer mixtures in which the oligomer contains several units from the series of carbohydrates and the carbohydrate is preferably glucose.

The invention also relates to oligomer or polymer mixtures in which the proportion of the viscous oligomer is, more particularly, between 5 and 95 percent by weight.

Moreover, the invention relates to oligomer or polymer mixtures in which the proportion of viscous oligomer is preferably between 30 and 70 percent by weight.

In addition, the invention relates to oligomer or polymer mixtures in which the proportion of viscous oligomer is, more especially, about 50%.

Additionally, the present invention relates to processes for preparing mixtures of oligomers and/or polymers based on lactic acid in which oligomers or polymers to be used for the mixture are prepared by methods known per se, mixed together, heated until they melt, the melt is homogenised and after being homogenised it is cooled and the semisolid mixture is isolated.

Furthermore, the present invention relates to the use of the oligomer or polymer mixtures according to the invention as an absorbable implant in the human or animal body and for the temporary filling of hard or soft tissue defects and, in particular, as absorbable bone wax and as a matrix material for the controlled release of active substances.

The objectives set out hereinbefore are achieved in particular by means of the examples which follow. Various embodiments of the process containing other and additional features associated with the present invention are set out in the specification for those skilled in the art and will be more readily understood in conjunction with the Examples which illustrate the currently preferred embodiments of the invention by way of example. However, it is expressly pointed out that the Examples and the associated specification are provided solely for the purposes of explanation and description and should not be regarded as limiting the invention.

EXAMPLES

Preliminary Remarks

Unless otherwise stated, the molecular weights given denote the number average molecular weight ($M_N$) determined by titration of the carboxylic end groups. In the Tables the number average molecular weight is given as a subscript.

EXAMPLE 1

Oligo(L-lactate), $M_N=315$

A 4 liter reaction flask with a blade stirrer, distillation bridge and dephlegmator is filled with 3030 g of L-lactic acid (90%) and evacuated with stirring to about 20 Torr (26.664 mbar). The reaction mixture is heated to 140° C. The water is distilled off over a period of 5.5 hours. During this time the temperature is increased to 150° C. After the reaction the oligomer melt is poured out and left to cool.

The condensation product has a molecular weight of 315. At ambient temperature it is highly viscous, fluid and transparent. There are no indications of crystallisation.

EXAMPLE 2

Oligo(L-lactate), $M_N=860$

This is prepared analogously to Example 1 except that the reaction time is 17 hours. Crystallisation of the oligomer begins during the cooling process. The molecular weight of the oligomer is 860. It is a hard solid having a melting point of 113° C. (DSC, heating rate 5K/min).

EXAMPLE 3

Oligo(D-lactate), $M_N=345$

This is prepared analogously to Example 1, except that 90% D-lactic acid is used. The molecular weight is 345. As with the condensation product of Example 1 it is an amorphous, highly viscous material.

EXAMPLE 4

Oligo(L-lactate), $M_N=547$ (comparative example)

A small sample is taken from the reaction mixture in Example 1 after a condensation time of about 10 hours and this sample is analysed. The molecular weight is 547. The product is transparent and hard as glass at ambient temperature but still flowable. Even after 3 weeks' storage at ambient temperature no crystallisation occurs.

EXAMPLES 5 TO 7

Mixtures of oligo(L-lactate) and oligo(D-lactate)

Mixtures are prepared from the oligomer of D-lactic acid described in Example 3 and oligomers of L-lactic acid with a molecular weight of 1815. The components required are weighed into a glass flask and then homogenised in a melt with stirring for a period of 15 to 30 minutes. The mixing temperature is 160° C. After homogenising the melt is poured out of the flask and left to cool. All the mixtures crystallise on cooling and become opaque.

| Composition* | | $M_N$ | Consistency | Example |
|---|---|---|---|---|
| $L_{1815}/D_{345}$ | | | | |
| 15 | 85 | 409 | waxy | 5 |
| 25 | 75 | 432 | waxy | 6 |
| 30 | 70 | 478 | waxy, slightly brittle | 7 |

*L and D respectively indicate an oligo- or poly-L- or poly-D-lactide (-lactate).

The mixture of Example 7 has a melting point of 148° C. (DSC, heating rate 5K/min).

EXAMPLES 8 TO 17

Mixtures of various oligo(L-lactides)

Mixtures are prepared from oligomers or polymers of L-lactic acid with various molecular weights. The tests are carried out analogously to Examples 5 to 7. The mixing temperature is 140° C. All the mixtures listed crystallise on cooling and become opaque.

| Composition* | $M_N$ | Consistency | Example |
|---|---|---|---|
| $L_{1815}/D_{315}$ | | | |
| 10 90 | 348 | soft, becomes ropey | 8 |
| 20 80 | 396 | waxy | 9 |
| 30 70 | 427 | waxy | 10 |
| 40 60 | 465 | waxy | 11 |
| 50 50 | 538 | waxy | 12 |
| 60 40 | 618 | waxy, slightly brittle | 13 |
| $L_{860}/L_{315}$ | | | |
| 50 50 | 451 | soft, becomes ropey | 14 |
| 70 30 | 557 | waxy | 15 |
| 80 20 | n.d.* | waxy | 16 |
| 90 10 | n.d.* | waxy, brittle | 17 |

*n.d. = not determined

The mixture of Example 12 has a melting point of 125° C. (DSC, heating rate 5K/min).

EXAMPLE 18

GPC Investigation of mixture 12

By way of example, GPC analysis was carried out on the mixture of Example 12 to find out whether there is any (partial) equilibration of the molecular weights during the melt mixing. As a comparison, a 1:1 mixture of the two starting components, prepared in solution, was used. GPC measurement was carried out using the following method:

Solvent: chloroform 0.5 mg per ml
Injection volume: 100 µl
Temperature: ambient temperature
Standard: narrow distributed polystyrene standard
Detector: RI-detector
Flow rate: 1 ml/min
Columns: PL-GEL columns 250/300/300 mm in the exclusion limits, 100, 1000, 100000 A.

Mixture 12: $M_W$=5690, $M_N$=2300, $M_W/M_N$=2.5
Comparison: $M_W$=5630, $M_N$=2280, $M_W/M_N$=2.5

I claim:

1. A bio-compatible, bio-absorbable material suitable for implantation into a warm-blooded animal and which is plastically deformable in a temperature range of from about 20° C. to about 40° C. which consists essentially of a crystalline polymer of D- or L-lactic acid or mixture thereof, which crystalline polymer has a number average molecular weight in the range of from about 600 to about 10,000 and an amorphous viscous oligomer of D- or L-lactic acid or mixtures thereof, which viscous oligomer has a number average molecular weight of less than about 500 and wherein the viscous oligomer constitutes about 5% to about 95% by weight of the bio-compatible, bio-absorbable material.

2. The bio-compatible, bio-absorbable material as recited in claim 1 which is a mixture of crystalline L-lactide and viscous L-lactide.

3. The bio-compatible, bio-absorbable material as recited in claim 1 wherein the crystalline polymer has a number average molecular weight in the range from about 800 to about 8,000 and the viscous oligomer has a number average molecular weight or less than about 400.

4. The bio-compatible, bio-absorbable material as recited in claim 1 wherein the crystalline polymer has a number average molecular weight in the range of from about 600 to about 10,000 and the viscous oligomer has a number average molecular weight of less than about 300.

5. The bio-compatible, bio-absorbable material as recited in claim 1 wherein the crystalline polymer has a number average molecular weight in the range of from about 1800 to about 4,000 and the viscous oligomer has a number average molecular weight of less than about 350.

* * * * *